United States Patent [19]

Wang

[11] Patent Number: 5,828,774
[45] Date of Patent: Oct. 27, 1998

[54] COMPUTER-AIDED DIAGNOSIS SYSTEM AND METHOD

[76] Inventor: Shih-Ping Wang, 409 Becker La., Los Altos, Calif. 94022

[21] Appl. No.: 579,802

[22] Filed: Dec. 28, 1995

Related U.S. Application Data

[63] Continuation of Ser. No. 129,255, Sep. 29, 1993, abandoned.

[51] Int. Cl.⁶ .................................................. G06K 9/00
[52] U.S. Cl. ...................... 382/128; 382/132; 364/413.22
[58] Field of Search .................................. 382/128, 132; 364/413.22; 128/431

[56] References Cited

U.S. PATENT DOCUMENTS

| | | | |
|---|---|---|---|
| 4,499,491 | 2/1985 | Aron et al. | 358/102 |
| 4,737,921 | 4/1988 | Goldwasser et al. | 395/135 |
| 4,833,625 | 5/1989 | Fisher et al. | 364/413.22 |
| 4,839,807 | 6/1989 | Doi et al. | 382/128 |
| 4,841,555 | 6/1989 | Doi | 378/98.4 |
| 4,851,984 | 7/1989 | Doi et al. | 382/108 |
| 4,875,165 | 10/1989 | Fencil et al. | 345/424 |
| 4,907,156 | 3/1990 | Doi et al. | 364/413.13 |
| 4,918,534 | 4/1990 | Lam et al. | 348/367 |
| 5,072,384 | 12/1991 | Doi et al. | 382/132 |
| 5,133,020 | 7/1992 | Giger et al. | 382/6 |
| 5,150,292 | 9/1992 | Hoffman et al. | 600/431 |
| 5,224,177 | 6/1993 | Doi et al. | 382/168 |
| 5,245,539 | 9/1993 | Romeas et al. | 382/132 |
| 5,331,550 | 7/1994 | Stafford et al. | 382/6 |
| 5,343,390 | 8/1994 | Doi et al. | 364/413.22 |

FOREIGN PATENT DOCUMENTS

| | | | |
|---|---|---|---|
| 2582819 | 12/1986 | France | G03B 21/100 |
| 3433141 | 3/1986 | Germany | G03B 42/02 |
| 3931531 | 4/1990 | Germany | A61B 5/00 |
| 2132353 | 5/1990 | Japan | G01N 23/18 |
| 91 07135 | 5/1991 | WIPO | A61B 6/12 |

OTHER PUBLICATIONS

Giger, et al., "An 'Intelligent' Workstation for Computer-aided Diagnosis," RadioGraphics, vol. 13, No. 3, May 1993, pp. 647–656.

Giger, et al., "Development of a 'smart' workstation for use in mammography," Proceedings of SPIE, vol. 1445, Immage Processing, 1991, pp. 101–103.

Specht, D.F., "Probabilistic Neural Networks," Neural Networks, vol. 3, 1990, pp. 109–118.

Wu, Y., et al., "Computerized detection of clustered microcalcifications in digital mammograms: Applications of artificial neural networks," Med. Phys. 19 (3), May/Jun. 1992, pp. 555–560.

Wu, Y., et al., "Artificial Neural Networks in Mammography: Application to Decision Making in the Diagnosis of Breast Cancer," Radiology, vol. 187, No. 1, Apr. 1993, pp. 81–87.

Yoshimura, H., et al., "Development of high quality film duplication system using a laser digitizer: Comparison with computed radiography," Med. Phys. 20 (1), Jan./Feb. 1993, pp. 51–58.

(List continued on next page.)

*Primary Examiner*—Christopher S. Kelley
*Attorney, Agent, or Firm*—Cooper & Dunham LLP

[57] ABSTRACT

X-ray images are displayed at both high-resolution and high-illumination with annotation superimposed in registration therewith to point out suspected abnormalities identified through a process in which the x-ray images are digitized and the digitized information is subjected to feature extraction processing. For example, the x-ray images are displayed at high resolution and high illumination in the form of x-ray film images displayed on a light box while the annotation information is selectively superimposed on the same image by a separate imaging system co-acting with the light box. In this manner, the radiologist can view either the x-ray film alone, in the conventional manner, or the same x-ray film, at the same position and at the same high resolution and at the same or substantially the same illumination level but with annotation information superimposed and in registration therewith. In addition, alternative ways are disclosed for displaying the high resolution x-ray image and for selectively superimposing the annotation information thereon.

24 Claims, 4 Drawing Sheets

SIDE VIEW OF FILM ILLUMINATOR
WITH A BACK PROJECTOR

OTHER PUBLICATIONS

Randall, T., Varied Mammogram Readings Worry Researchers, Journal of the American Medical Association, vol. 269, No. 20, May 26, 1993, pp. 2616–2617.

Gonzales, R.C., et al., "Digital Image Processing," published by Addison–Wesley, Nov. 1987 pp. 233–239.

Russ, John C., "The Image Procesing Handbook," CRC Press, Inc., 1992 Table of Contents.

SCHEMATIC DIAGRAM OF THE CAD SYSTEM

CRANIOCAUDAD (CC) VIEW MAMMOGRAM

LATERAL (MLO) VIEW MAMMOGRAM

SIDE VIEW OF FILM ILLUMINATOR
WITH A BACK PROJECTOR

COMPUTER-AIDED DIAGNOSIS SYSTEM AND METHOD

This is a continuation of application Ser. No. 08/129,255 filed Sep. 29, 1993 now abandoned.

FIELD AND BACKGROUND OF THE INVENTION

The invention is in the field of x-ray technologies and specifically relates to displaying x-ray images in a manner that is believed to assist in reading x-ray images. More specifically, the invention relates to displaying x-ray images together with annotation information derived by computer-aided analysis of the images. Still more specifically, the invention relates to a computer-aided diagnosis system and method for the detection of abnormalities from a digitized radiologic image and the production of a separate annotated map of the location of detected abnormalities for the purpose of annotating the radiologic image in a manner enabling the observer to view the film x-ray image, or an image of a comparable high resolution, together with the annotated map without taking his or her eyes off the x-ray film and at an illumination level which is the same as or is comparable with that provided by a conventional light box. More specifically, the invention pertains to a computer-aided diagnosis system and method which improve diagnostic efficiency and accuracy by adding particularly convenient annotation to the original radiologic image.

The detection of abnormal anatomic regions in radiologic images using a computer system using specialized software and possibly hardware components has been reported by, e.g., Giger et al. in May 1993 issue of RadioGraphics, pages 647–656; Giger et al. in Proceedings of SPIE, Volume 1445 (1991), pages 101–103; Doi et al in U.S. Pat. No. 4,907,156; and Giger et al. in U.S. Pat. No. 5,133,020. These and the other references cited below in this patent specification are incorporated herein by reference as though fully set forth herein. These systems are generally referred to as Computer-Aided Diagnosis systems, or CAD systems, and are believed to be particularly useful to radiologists in the diagnostic process and particularly in screening radiologic procedures.

In a screening radiologic procedure, such as screening mammography, the patients typically are asymptomatic and true abnormalities (e.g. cancers) are believed to occur at a typical rate of about one case per one hundred patient examinations. Reading the mammograms, when most of them are negative, can be a tedious task that makes it difficult to maintain a consistently high attention level. Some detectable abnormalities can be missed or misdiagnosed, which can result in delayed or more difficult or more costly treatment, and can even result in a reduction of patient's chance of survival. According to an article in the May 26, 1993 issue of JAMA, pages 2616–2617, the misdiagnosis rate in mammograms can be in the range of 15 to 63%. It is believed that the CAD Systems, serving as an electronic reminder or second reader, can assist radiologists in obtaining higher detection rate (higher sensitivity) for abnormalities or in reducing the misdiagnosis rate (lowering the false-negative rate).

It is believed that a current procedure using a CAD system proceeds as follows. The radiologist views a radiologic image and reaches a preliminary diagnostic decision, and then views a separate second image displayed on a CAD system. This second image has marked or annotated thereon the abnormalities that the CAD system detected. After reviewing the CAD-detected abnormalities, the radiologist makes the final diagnostic decision, which may or may not be the same as the preliminary decision because it can depend on whether additional diagnostic information was provided by the CAD system. Following the final diagnostic decision, and perhaps depending on the degree of suspicion for malignancy, the radiologist can recommend a course of further action which can include further follow-up examinations or biopsy.

In the process of detecting abnormal anatomic features in radiologic images using a CAD system as described in the above cited references, the radiologic film image of a patient is processed through a film digitizer to generate a digitized image which is input as such into the system. The digitized image is then analyzed by a digital image processing computer with specialized software and perhaps hardware for abnormal anatomic feature detection. If abnormalities are detected, an annotated radiologic image is displayed on a special TV monitor, with markers placed around or adjacent the detected abnormalities. This TV monitor typically has high spatial resolution (typically greater than 1000×1000 pixels) but, because of the high spatial resolution requirement, typically has low brightness (typically less than 100 foot-lamberts)

While the above described COD system can point out the CAD-detected abnormalities to the radiologist, it is believed that the display method that it utilizes has certain shortcomings, such as inconvenience and inefficiency of the process of using it, the relatively high cost of a high-resolution TV monitor and its reduced spatial resolution as compared with the higher spatial resolution of the original x-ray film, and relatively low brightness and dynamic range of the high-resolution TV monitor as compared with the brightness of an x-ray film viewed on a light box and the dynamic range of a light box display/x-ray film. Therefore, it is believed that a radiologist typically would not rely solely on the image displayed on the TV monitor to make diagnosis, but would repeatedly go back to the conventional film illumination box to view the original film image, This can lead to the loss of valuable time and can be uncomfortable at least because of the different brightness levels and spatial resolution levels of the two images. In addition, it is believed that diagnostic errors can arise from the need for the radiologist to shuttle back and forth between the two different displayed images. Still additionally, it is believed that current CAD system treat the detected abnormalities in a manner that does not sufficiently differentiate between different types of abnormalities or different confidence levels that the detected abnormality is a true abnormality.

SUMMARY OF THE INVENTION

An object of the invention is to improve the display of combined x-ray images and CAD-detected abnormalities. A more specific object is to improve the convenience, accuracy and efficiency in the radiologist's viewing process by particularly effectively combining high-brightness display of the original high quality film image with an annotation map registered therewith. Another objective is to reduce the cost of equipment by using lower cost and widely available display equipment. Yet another object of the invention is to provide annotation information that can include an assessment of the probability or likelihood that the CAD-detected abnormalities have been correctly identified, as an additional aid to the radiologist.

In an exemplary and non-limiting first embodiment of the invention, an inexpensive TV monitor that has high brightness but low spatial resolution serves two functions: it displays an annotated map of the CAD-detected abnormalities and, at the same time, serves as a light box for a conventional film placed over its screen in registration with the displayed annotated map. The annotated map can be displayed selectively, under the radiologist's control, to provide the option of viewing the x-ray film alone or with the annotation map superimposed thereon. The annotation map can selectively provide additional information from the CAD system, such as the probability or likelihood of the detected abnormalities. This additional information can be displayed as a part of the annotation map, e.g., by suitable variation in the shape, size, or brightness of the displayed information identifying the CAD-detected abnormalities.

Because the TV monitor does not display the original x-ray film image but only illuminates it, the spatial resolution requirement of the TV monitor can be reduced substantially. Because the film image and the annotation map are selectively displayed overlaid on each other, and in registration with each other, a radiologist can make a diagnosis by looking at only one displayed image, namely, the original image, with the locations of abnormalities marked or highlighted thereon by means of the superimposed annotation map.

In another exemplary embodiment, discussed as a second embodiment herein, the annotated map is printed on a transparent plastic sheet. This transparent sheet can be placed over and in registration with the original radiologic film on a suitable illumination device, such as a conventional light box, to allow the radiologist to view selectively the x-ray film with the annotated map superimposed thereon.

In another exemplary embodiment, discussed herein as a third embodiment, the high brightness TV monitor of the first embodiment is replaced with a conventional film illuminator (light-box) modified by the addition of a back-projector. The back-projector selectively projects the annotation map onto the x-ray film, in registration therewith.

In another exemplary embodiment, discussed herein as a fourth embodiment, the high brightness TV monitor of the first embodiment is replaced with a conventional film illuminator modified by the addition of an addressable liquid crystal display (LCD) screen interposed between the film and the film illuminator for the purpose of selectively displaying the annotation map.

In still another exemplary embodiment, discussed therein as a fifth embodiment, a viewing station for the viewing of multiple x-ray films has a bank of film illuminators, each illuminator having its own provisions to display selectively an annotation map superimposed on a respective x-ray film.

Stated in broader terms, in one aspect the invention is embodied in a system or a process providing digitized image data representing x-ray images characterized by high spatial resolution, a processor receives said digitized image data and generate as a function thereof an annotation map identifying image portions meeting selected criteria, and a display displays said x-ray images for viewing at said high spatial resolution and at a high brightness level while selectively superposing thereon said annotation map in registration therewith.

In this context, the term high spatial resolution is used to mean a spatial resolution such as provided by x-ray film or such as provided by medical imaging devices which provide an image only in digital form such as, without limitation CT scanners or nuclear medicine cameras or scanners or other devices or systems. In some cases, identified as such in the specification and claims herein, the term high spatial resolution is used to mean spatial resolution at least at the level of that of x-ray film image. In still other cases, also identified as such, the term is used to mean spatial resolution comparable to that of x-ray film but higher than that of currently known medical imaging systems that provide the primary image data only in digital form.

The term high brightness level is used herein to mean higher brightness level than provided by currently known display devices that have high spatial resolution, such as those used in the known process discussed above of using a high spatial resolution monitor to display a single, composed image that shows both a digitized version of an x-ray film and annotation markings for that film In special cases identified as such, the term is used to mean brightness at the level of that provided by known illumination boxes (light boxes) used by radiologists. In still other cases identified as such, the term is used to mean brightness at levels such as provided by low spatial resolution (e.g., NTSC or PAL spatial resolution or comparable or lower spatial resolution) conventional TV monitors or computer terminal monitors.

DETAILED DESCRIPTION

Figure 1:
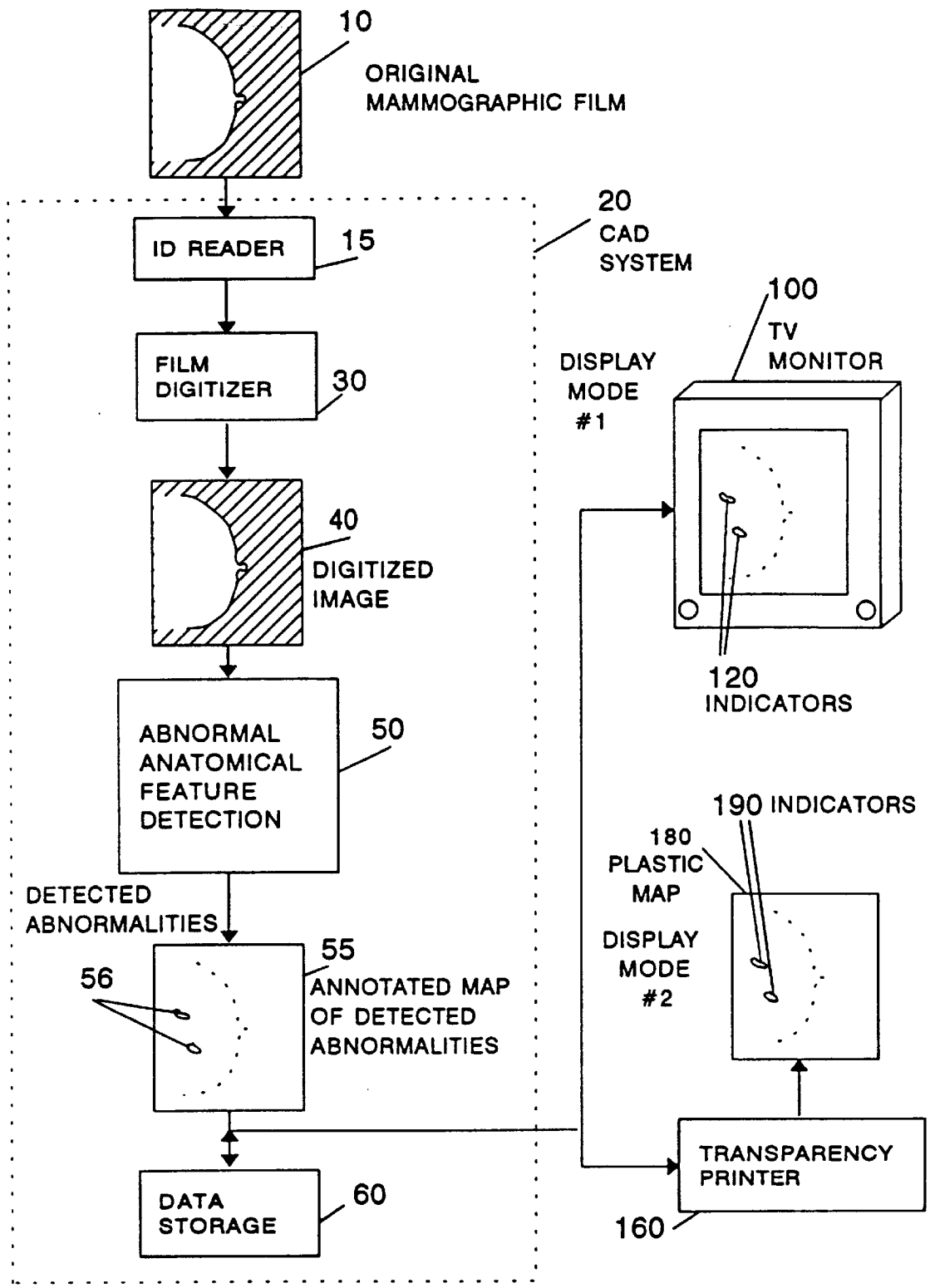
FIG. 1 is a schematic diagram illustrating a CAD system and two output display modes according to first and second embodiments of the invention.

Referring to FIG. 1, a preferred but non-limiting example of the invention generates an annotation map of CAD-detected abnormalities and selectively displays it in registration with an x-ray film image. In this example, the radiologic image is in the form of a mammographic x-ray film acquired with a conventional mammographic film-screen imaging system. The original analog two-dimensional mammographic x-ray film 10 is digitized with a film digitizer 30 of a CAD (computer-aided diagnosis) system 20 (such as that disclosed in said U.S. patents which are incorporated by reference herein) to obtain a digitized two-dimensional mammographic image 40. Preferably, the film digitizer 30 should be a laser film digitizer and should have dynamic range and spatial resolution comparable to those of the original mammographic film which typically has a dynamic range of 10,000:1 and spatial resolution of approximately 50 microns per pixel (or about 4,000×4000 pixels per image). The identity of the original mammographic image 10 is also entered into CAD system 20 at this point to identify the digitized mammographic image 40. An useful option at this point is to automatically input the identity of this original mammographic image 10 into CAD system 20. This can be accomplished, for example, by first labelling the mammographic film 10 with a code such as a bar code, and then reading the label into CAD system 20 with an optional ID bar code reader 15 as the mammographic film 10 is being fed into film digitizer 30.

Certain radiologic images may already be in the digital format, such as images were acquired with a digital imaging system in the form of a computed tomography system, an ultrasound imaging system, a scintillation camera, a digital stimulated emission phosphor plate radiography system such as Fuji's Computed Radiography or recently reported digital mammographic systems using CCDs, or some other digital imaging system. Such digitized images can be directly entered in CAD system 20 as the digitized image 40 and the initial film digitization step is not needed in this case.

The digitized mammographic image 40 is then sent through the abnormal feature detection stage 50 of CAD machine 20. The findings or results, positive or negative in nature, from abnormal feature detection stage 50 are in the form of a two-dimensional annotation map 55, or x–y coordinate information, of the locations of CAD-detected abnormalities in original film image 10. The CAD-generated annotation map 55 can be stored for later use in an optional memory storage unit 60, together with the digitized image 40 and its corresponding identification. This annotation map 55 is then transferred to the output display section of the system for display, for example in accordance with the illustrated display mode #1 and display mode #2.

As shown in FIG. 1, mode #1 for displaying the annotation map 55 involves scaling the annotation map 55 to the same size as the original film image 10, and displaying the so-scaled annotation map 55 on a high brightness and low spatial resolution TV monitor 100. The location of the detected abnormalities is marked on the displayed annotation map 50 with indicators 120. The original x-ray film can be placed over the screen of TV monitor 100, in registration with the scaled annotation map 55, so that the monitor can serve the role of a conventional light box and the radiologist can view the x-ray film image 10 and the annotated map 55 as a single composite image, or can turn off the display of the annotation map 55 and selectively view only the x-ray image. Also as illustrated in FIG. 1, display mode #2 involves printing the annotation map 55, scaled to the same size as the original film image 10, on a transparent plastic sheet 180 with a transparency printer 160. The location of the detected abnormalities is marked with indicators 190. In both cases, additional registration aids can be provided in the annotation map 55, such as registration marks, to ensure reasonable registration between the displayed annotation map 55 and the radiologic film 10. These additional registration aids can be in the form of notches on edges of map film 180 that match the notches of the original film 10 or they can be in the form of printed outlines of the nipple and skin line 56a (FIG. 1) of the imaged breast.

The TV monitor display device 100 in the example illustrated in FIG. 1 is a high brightness (over 400 foot-lamberts for radiologic images such as chest and preferably above 1000 foot-lamberts for mammography) and low spatial resolution (less than 200×200 pixels of spatial resolution) TV monitor. This TV monitor 100 only displays the annotation map 55 of locations of the detected abnormalities of the radiologic film by marking the locations with indicators 120.

The purpose of indicators such as 120 and 190 is to draw the radiologist's attention to the indicated area Typical indicators 120 and 190 are in the form of a box, an arrow, a circle or some other pointer at or in the vicinity of the CAD-detected abnormality, or in the form of a spot having a brightness slightly higher or lower (say, equivalent to a net density change of about 0.1) than the background field. The size of an indicator such as 120 and 190 can be about 1.5 to 2.0 times larger than the size of the indicated CAD-detected abnormality. Because typical abnormalities in mammography tend to be relatively small, such as minimal cancers with a diameter of less than one inch, typical indicator size can be about two inches in size. The size of the indicator may be enlarged in cases where the size of the detected abnormality is larger than one inch or is expected to be larger than an inch. In this case, the required registration precision between the displayed annotation map 55 and the radiologic film 10 is about half inch, i.e., the size of the margin between the detected abnormality and the indicator.

Figure 2A:
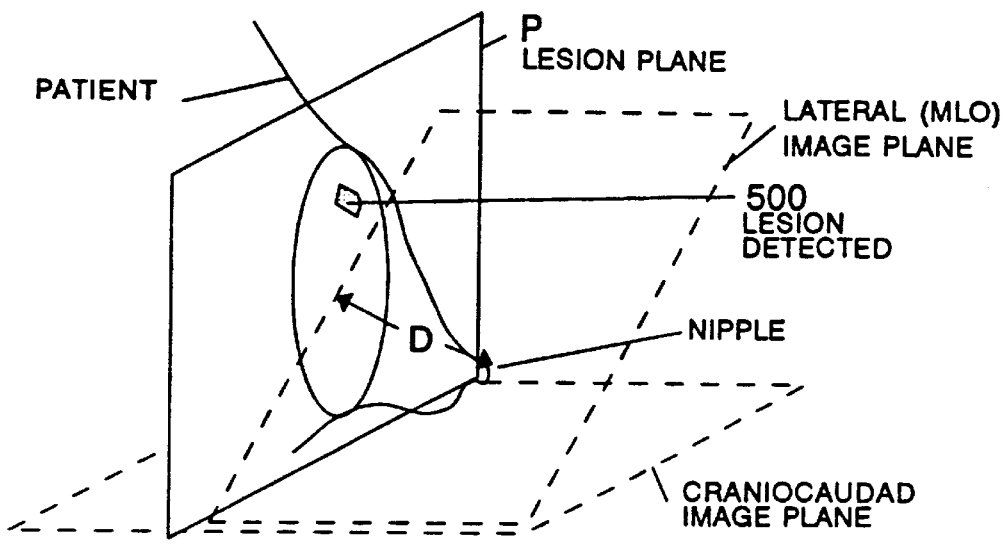
FIG. 2A shows a lesion plane P which is located at a distance D from the nipple of an imaged breast and is orthogonal to both the craniocaudad and the lateral image planes.
Figure 2B:
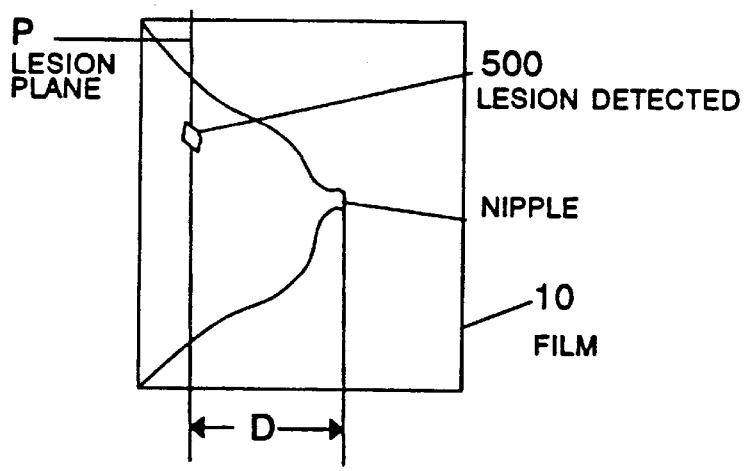
FIG. 2B shows the craniocaudad view and the lesion plane P appearing as a line located at a distance D from the nipple.
Figure 2C:
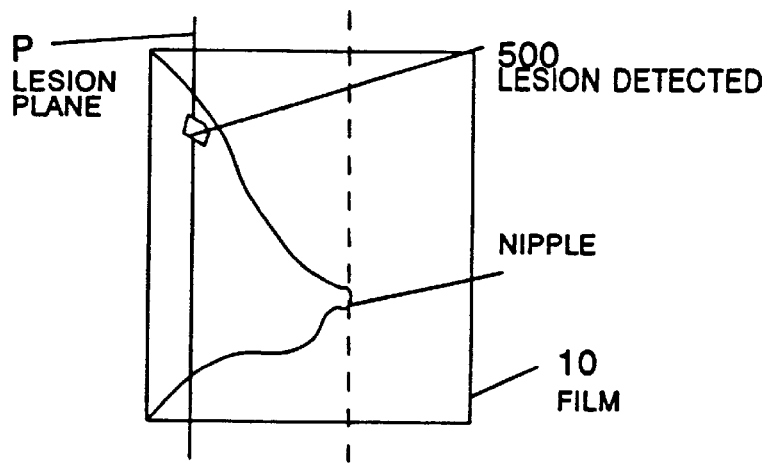
FIG. 2C shows the lateral view and the lesion plane P appearing as a line located at a distance of D from the nipple

The displayed indicators 120 and 190 alternately can comprise additional information from the CAD system 20 such as the probability or likelihood of the detected abnormalities being a true abnormality or having some selected parameter. This additional information can be displayed by appropriately modifying the indicator's shape, size, border width, and/or brightness levels, or by displaying additional lettered annotations. The probability or likelihood of the detected parameter of the CAD-detected abnormality can be obtained in the following manner, as a non-limiting example. In mammography, each breast is usually imaged twice; the first image is called the craniocaudad (CC) view, and the second image is a lateral view, usually the mediolateral oblique (MLO) view. If the same number of abnormalities is detected in both views of the same breast, or it similar types of abnormalities are detected in both views of the same breast, or if any one pair of similar type of abnormalities in both views of the same breast are detected in the same lesion plane which is orthogonal to both the craniocaudad and the lateral image planes and is defined by its distance from the nipple, as illustrated in FIGS. 2A–2C, then the detected abnormality can be assigned a probability and can be displayed with indicators with added emphasis In certain image pattern classification methods, such as the probabilistic neural networks described by Specht in an article in Neural Networks, volume 3 (1990), pages 109–118, entitled "Probabilistic Neural Networks," the probability of a detection can be estimated. Therefore, using such image pattern classification methods in a CAD system such as system 20, one can obtain additional information on the probability of a detection. Wu et al. described methods for using neural networks technique in mammographic CAD systems in the following two articles: (1) Medical Physics, Volume 19 (1992), pages 555–560; and (2) Radiology, volume 187 (1993), pages 81–87.

Figure 3:
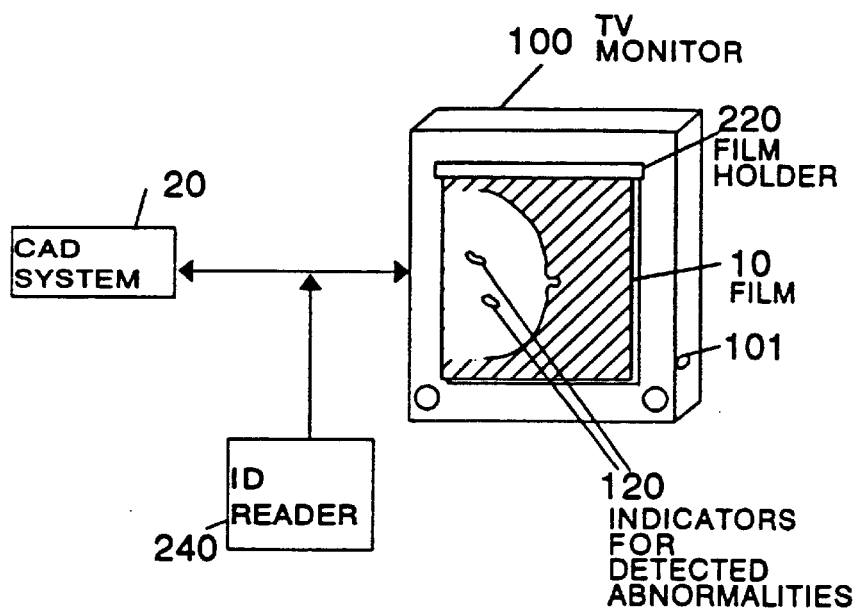
FIG. 3 illustrates an x-ray film illuminated by a TV monitor which selectively displays an annotation map pointing out CAD-detected abnormalities according to the first embodiment of the invention.

FIG. 3 illustrates in greater detail certain aspects of the first embodiment of the invention, i.e., annotating the original radiologic film 10 by placing it on the TV monitor 100, over the selective display of the annotation map 55. An optional film holder 220 is provided on one edge of the TV monitor 100 for the purpose of holding the radiologic film 10 by its edge to the TV monitor 100, in registration with the annotation map 55. Film holder 220 can be similar to the film holders used in conventional light boxes for viewing x-ray film, and can have sufficient room for manually adjusting the position of x-ray film 10 relative to the displayed annotation map 55 in order to achieve sufficient registration. The CAD-detected abnormalities are marked by indicators 120 on the TV monitor 100. In this case, the TV monitor 100 is used in place of the conventional light box to illuminate the original radiologic film 10 and is used, additionally, to display selectively the locations of the CAD-detected abnormalities marked by indicators 120. Thus, a radiologist can now make a diagnosis by looking at only one composite displayed image, namely, the original film 10, with the locations of abnormality marked or highlighted by indicators 120 on the TV monitor 100. This arrangement also allows the observer or radiologist to go back and forth between the annotated and non-annotated images conveniently and simply by toggling a display switch 101, which turns the annotation map 55 on and off while keeping the monitor 100 on so that it can continue serving as an illuminating light box.

TV monitor 100 should have high brightness in order to serve the function of a light box. However, it does not need to he a high resolution monitor because it is not displaying the x-ray image but only the annotation information which need not be at high spatial resolution. Accordingly, the spatial resolution requirement of the TV monitor can be reduced substantially. Thus, a relatively inexpensive TV monitor can be used in this embodiments. TV monitor 100 can be pre-calibrated with test films so that misregistration between x-ray image 10 and annotation image 55, if any, is minimized. An optional ID reader 240, in the from of a bar code reader for example, can be used to identity the original film 10 and to call up from data storage unit 60 (shown in FIG. 1) the locations of the detected abnormalities, and any other annotation information, for the same film for display on the TV monitor 100.

Using the CAD System in some ways as a second reader, the radiologist can first review the original x-ray film 10 on the TV monitor 100 (without at that time displaying the annotation image 55) and can make a preliminary diagnostic decision. During this first viewing, the TV monitor 100 simply operates as a film illuminator and no indicators such as 120 are displayed. Then, without moving the original film 10 from the TV monitor 100, the radiologist activates switch 101 to turn on the display of the annotation map 55 and thereby display indicators 120 to mark the CAD-detected abnormalities for the same original film 10. After viewing the original film 10 with the detected abnormalities marked by indicators 120, the radiologist can make the final diagnostic decision, which may or may not be same as the preliminary decision and can be influenced by additional diagnostic information provided by the CAD-detected abnormalities. The radiologist can go back and forth between the annotated and non-annotated images, without taking his or her eyes off the x-ray film, simply by toggling switch 101 to turn on and off the display of annotation map 55.

Figure 4:
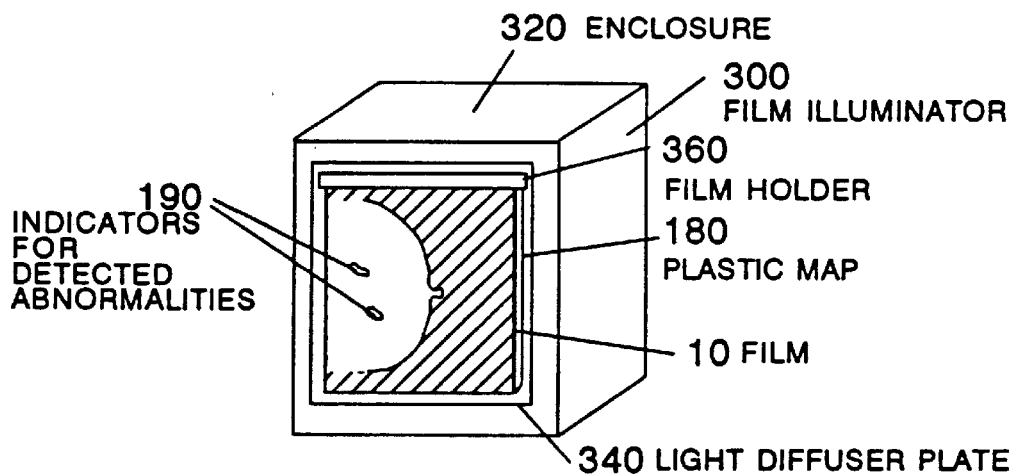
FIG. 4 illustrates the display of an x-ray film and an overlaid transparency print of an annotation map according to the second embodiment of the invention.

FIG. 4 illustrates in greater detail another mode, namely, mode #2 referred to earlier in connection with FIG. 1 a an alternative annotation display in the form of a transparent plastic sheet 180 with the indicators 190 printed on it to mark the locations of CAD-detected abnormalities. In the embodiment illustrated in FIG. 4, the original radiologic film 10 is placed in superposition and registration with the transparent plastic map 180. The radiologist views both images as a single composite image on a conventional film illuminator (light box) 300. Such a conventional film illuminator 300 usually has an enclosure 320, a translucent plastic light diffuser plate 340 as the front window, a film holder 360 on the top edge of the film illuminator 300 for the purpose of holding the radiologic film 10 and the transparent plastic map 190 by their top edges to maintain good registration, and a light source in the form of fluorescent lamps. The transparent plastic annotation map 180 may be placed behind the original film 10 (i.e. between the original film 10 and the film illuminator 300) or in front of the original film 10 The transparent plastic annotation map 180 can be pre-calibrated or cut to the same size as the original film 10 to minimize misregistration with the original film 10.

Figure 5:
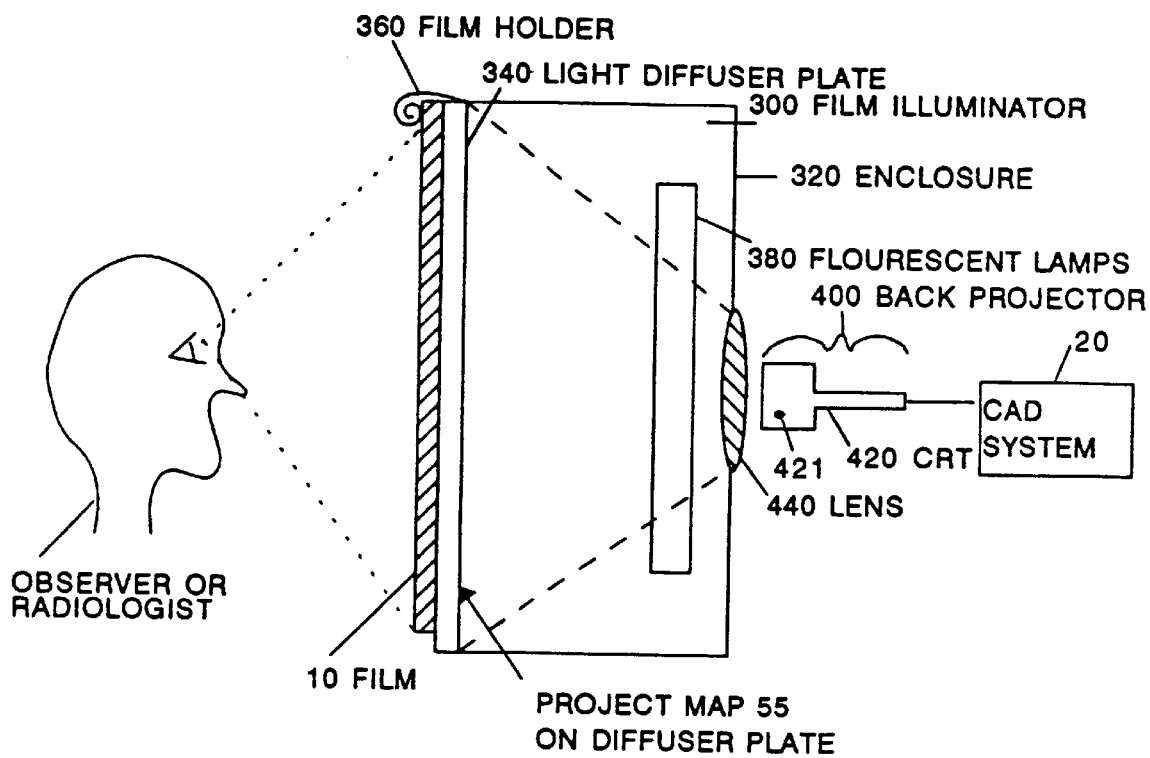
FIG. 5 is a partly sectional side view illustrating a film illuminator having a back-projector according to a third embodiment of the invention or having an LCD screen according to a fourth embodiment of the invention.

FIG. 5 illustrates a third embodiment of the invention, in which the original film 10 is annotated selectively by means of a light box modified by the addition of a back projector for the annotation map 55. In particular, conventional film illuminator 300 is modified by the addition therein of a back-projector 400 Film illuminator 300 has an enclosure 320, a translucent plastic light diffuser plate 340 as the front window, a film holder 360 on the top edge of the film illuminator 300, and a light source in the form of fluorescent lamps 380, The annotation map 55, which is obtained as x–y address information or a video signal from the CAD system 20 in a manner similar to that discussed in connection with TV monitor 100 in FIG. 1, is back-projected by the back-projector 400 onto the front light diffuser window 340. The original film 10 is placed against the light diffuser window 340, in the conventional manner, for diagnostic reading and the image of the annotation map 55 can be toggled on and off with the back projector 400 by manually operating a switch 421 at a back-projection CRT 420. The back-projector 400 can comprise a high intensity CRT 420 and a lens and/or mirror projection system 440. Instead of the high intensity CRT 420, back projector can use a high intensity lamp, a heat-removing filter and a low spatial resolution (about 200×200 pixels or less) addressable liquid crystal display (LCD) screen, which is capable to receive and display the annotation map 55 on command from the CAD system 20.

The fourth embodiment of the invention is also illustrated in FIG. 5 (schematically) and is yet another arrangement to annotate the original film 10 by replacing the high brightness TV monitor 100 of the first embodiment with a conventional film illuminator and an added low spatial resolution (about 200×200 pixels or less) addressable liquid crystal display (LCD) screen interposed between the original film 10 and the conventional film illuminator 300. This addressable liquid crystal display (LCD) screen 480, which is the same size as the light diffuser window 340, may also take the place of the light diffuser window 340. In this fourth embodiment, the back-projection system illustrated in FIG. 5 is not used.

Figure 6:
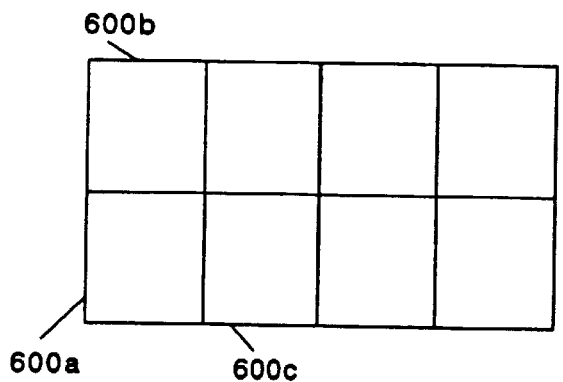
FIG. 6 illustrates a fifth embodiment of the invention using a bank of film viewers each of which can be in accordance with any one of the first through fourth embodiment.

FIG. 6 illustrates still another embodiment, the fifth embodiment, in which a viewing station or an alternator (a multiviewer having but not showing pre-loaded films and a transport belt) allows several x-ray films 10 to be viewed at the same time or at different times, with or without their respective annotation maps 55. The fifth embodiment comprises a bank of film illuminators 600*a,* 600*b,* etc., each illuminator having its own provisions to illuminate the original film 10 and display the corresponding annotation map 55. Each illuminator of the bank may be constructed in accordance with any one of the above described four different illumination/display embodiments. The illuminators in the bank illustrated in FIG. 6 can be of the same kind, or different illuminators in the bank can be in accordance with different ones of the four embodiments discussed above.

In FIG. 2A, the lesion plane P, which contains a lesion 500, is located at a distance D from the nipple of the imaged breast and is orthogonal (perpendicular) to both the cranio-caudad (CC) and the lateral (MLO) image planes. For convenience of illustration, this plane is also chosen to be perpendicular to the short edges of the film 10. Therefore, the lesion plane P appears as a line located at a distance D from the imaged nipple and perpendicular to the short edges of the film in both the craniocaudad (CC) view in FIG. 2B and in the lateral (MLO) view in FIG. 2C of the same breast. If a lesion of similar type or characterization (e.g., cluster of microcalcifications, spiculated mass, etc.) is detected in each of the two views of the same breast and if these two lesions are in the same lesion plane, as defined above, then a higher probability marker can be assigned to this detected lesion than for a lesion detected in only one of the two views of the same breast.

The CAD system 20 with the above described display can be used, alternatively, by radiologic technologists to check for abnormalities as an additional aid to radiologists. For example, such a check can be carried out before discharging the patient from the facility so that, if significant abnormalities are detected at that stage, the technologist can take additional views or magnification views in order to better characterize the CAD-detected abnormalities. These additional views may provide sufficient information to the radiologist to make a patient recall unnecessary and thus reduce the expense and patient anxiety that can be associated with patient recalls.

In some circumstances, a radiologists may wish to use a conventional film illuminator only, without using any of the above described four display systems for the annotated map. In this case, a high spatial resolution film printer can be used to print both the radiologic image and the annotated map of the locations of detected abnormalities on the same sheet of a high spatial resolution film. The radiologist may choose to view the annotated film side-by-side with the non-annotated film or may choose to view the annotated film only. In the latter case, the original image quality can be preserved by printing the annotated film at a high spatial resolution, for example, 50 microns or less per pixel for mammograms and other single screen techniques and 100 microns or perhaps less per pixel for chest films and other double screen techniques (about 4000×4000 pixels or better). Additionally, image enhancements can be provided in the digitized image 40 before printing out the annotated film, such as by using the enhancement techniques described in a book by Gonzales and Wintz, entitled: "Digital Image Processing" published by Addison-Wesley 1987.

Although the invention has been described in terms of preferred structures and processes, it should be apparent to those skilled in the art that various alterations and modifications can be made without departing from the invention and that such modification and alterations are intended to be considered to be within the spirit and scope of the invention as defined by the appended claims.

I claim:

1. A system comprising:
    a source of digitized image data representing x-ray film said digitized image data having a selected spatial resolution;
    a processor coupled with said source to receive said digitized image data, to process said data to detect abnormal anatomical features meeting selected criteria and to generate annotation maps identifying image portions corresponding to said abnormal anatomical features; and
    a display coupled with said processor and illuminating said x-ray film for viewing at full analog spatial and contrast resolution while selectively electronically displaying in association therewith corresponding annotation maps at a lower spatial resolution than said selected spatial resolution of said digitized image data, at positions in space which are spatially matched to said illuminated x-ray film.

2. A method comprising the steps of:
    providing x-ray film and generating therefrom digitized image data having a selected spatial resolution;
    computer-processing said image data to generate respective annotation maps for said x-ray film through an image analysis process identifying anatomical abnormalities at image portions meeting selected criteria; and
    illuminating said x-ray film for viewing at full analog spatial and contrast resolution, and concurrently electronically displaying said respective annotation maps at a lower spatial resolution than said selected spatial resolution of said image data, at positions in space corresponding to those of said illuminated x-ray film.

3. A system as in claim 1 in which said source comprises a digitizer processing said x-ray film to provide said digitized image data in a display format exceeding 3000×3000 pixels.

4. A system as in claim 3 in which said display comprises a relatively low spatial resolution monitor which selectively displays said annotation maps and serves as a light box for said illuminating of said x-ray film.

5. A system as in claim 4 in which said monitor comprises a switch under the control of an observer for selectively turning on and off the display of said annotation maps while said illuminating of said x-ray continues.

6. A system as in claim 3 in which said display comprises an x-ray film light box for viewing said x-ray film and an annotation map source co-acting with said light box to selectively display said annotation maps.

7. A system as in claim 6 in which said annotation map source comprises a CRT displaying said annotation maps and projection optics coupling optically said CRT and said light box to superimpose respective ones of said annotation maps on said x-ray film.

8. A system as in claim 6 in which said x-ray film light box comprises a light source illuminating the x-ray film being viewed and said annotation map source comprises a display screen displaying said annotation maps positioned between the light source and the x-ray film to project the annotation maps for selective superposition on the x-ray film being viewed.

9. A system as in claim 8 in which said display screen displaying said annotation maps serves as a diffuser screen for said light box.

10. A system as in claim 8 in which said display screen displaying said annotation maps comprises a liquid crystal display (LCD) screen.

11. A system as in claim 1 in which said x-ray film comprises mammographic film and said processor includes a skin line in said annotation maps.

12. A system as in claim 1 comprising a bank of display units each comprising a respective display and wherein said processor is coupled with the respective displays to selectively display thereon respective annotations maps in selected spatial relationships with said x-ray film.

13. A method as in claim 2 in which said step of generating said x-ray image data comprises digitizing said x-ray film to generate said digitized image data at a spatial resolution of 100 microns or less per pixel.

14. A method as in claim 2 in which said step of computer processing comprises generating said annotation maps at a spatial resolution of 100 microns or more per pixel.

15. A method as in claim 2 in which said illuminating comprises illuminating said x-ray film with a low spatial resolution monitor which selectively displays said annotation maps in registration with the illuminated x-ray film.

16. A method as in claim 14 in which said illuminating comprises illuminating said x-ray film for viewing with a light box.

17. A method as in claim 2 in which said step of computer-processing comprises processing mammographic x-ray film to generate annotation maps showing a breast skin outline and said step of electronically displaying said annotation maps includes displaying said breast skin outline at a selected spatial relationship to said x-ray film.

18. A method as in claim 2 which said step of computer-processing comprises generating measures of confidence levels in the identification of said anatomical abnormalities, and said step of displaying comprises displaying indications of said measures of confidence in said annotation maps.

19. A method as in claim 2 in which said step of providing said x-ray film includes labeling said film with a bar code, reading said bar code with a bar code reader in connection with providing said digitized image data, and electronically storing said bar codes together with said annotation maps for later use.

20. A system as in claim 1 in which said x-ray film has bar code identifications, said source of digitized image data comprises a bar code reader reading said bar code identifications, and said processor receives said bar code identifications and stores them electronically in association with said annotation maps for later use.

21. A method as in claim 2 in which said annotation maps comprise markers indicative of abnormalities which meet respective probability thresholds.

22. A method as in claim 2 in which said annotation maps comprise respective different markers for each different type of a selected set of abnormalities.

23. A method as in claim 2 including printing said annotation maps to provide a hard copy printed record thereof.

24. A method as in claim 2 including selectively processing said digitized image data to image-enhance one or more of said image portions thereof.

* * * * *

Disclaimer

5,828,774—Shih-Ping Wang, Los Altos, Ca. COMPUTER-AIDED DIAGNOSIS SYSTEM AND METHOD. Patent dated October 27, 1998. Disclaimer filed June 6, 2002 by the inventor Shih-Ping Wang.

The term of this patent shall not extend beyond the expiration date of Pat. No. 5,729,620.

*(Official Gazette, August 27, 2002)*